United States Patent [19]

Fischer et al.

[11] Patent Number: 4,568,331

[45] Date of Patent: Feb. 4, 1986

[54] DISPOSABLE MEDICINE DISPENSING DEVICE

[76] Inventors: Marcus Fischer, 2609 SW. 23rd Cranbrook Dr., Boynton Beach, Fla. 33436; Robert Campitelli, 603 NW. 7th Ct., Boynton Beach, Fla. 33435

[21] Appl. No.: 542,484

[22] Filed: Oct. 17, 1983

[51] Int. Cl.[4] .............................................. A61M 31/00

[52] U.S. Cl. ........................................ 604/56; 604/85; 604/92; 206/221

[58] Field of Search .............................. 604/56, 82-86, 604/283, 241, 416, 92, 185; 206/219, 221; 128/DIG. 24

[56] References Cited

U.S. PATENT DOCUMENTS

| | | | |
|---|---|---|---|
| 2,907,325 | 10/1959 | Burke | 604/185 |
| 3,001,525 | 9/1961 | Hendricks | 604/416 |
| 3,021,841 | 2/1962 | Burke | 604/185 |
| 3,142,074 | 7/1964 | Reich | 128/DIG. 24 |
| 3,921,635 | 11/1975 | Gauthier | 604/84 |
| 4,240,428 | 12/1980 | Akhavi | 604/241 |
| 4,340,148 | 7/1982 | Beckham | 604/241 |
| 4,392,851 | 7/1983 | Elias | 604/416 |
| 4,453,929 | 6/1984 | Silverman et al. | 604/56 |

FOREIGN PATENT DOCUMENTS

| | | | |
|---|---|---|---|
| 2921565 | 12/1980 | Fed. Rep. of Germany | 604/82 |

*Primary Examiner*—C. Fred Rosenbaum
*Assistant Examiner*—Michelle N. Lester
*Attorney, Agent, or Firm*—Silverman, Cass & Singer, Ltd.

[57] ABSTRACT

A medication dispensing device for administering medicine to patients unable to swallow includes a flexible chamber in which solid medicinals, such as tablets, can be pulverized and dissolved or placed in suspension in a liquid medium which thereafter can be administered to the patient from the chamber through an elongate feeding tube through the mouth or nose.

7 Claims, 4 Drawing Figures

DISPOSABLE MEDICINE DISPENSING DEVICE

BACKGROUND OF THE INVENTION

This invention generally relates to medicine dispensing devices, and more particularly, relates to devices for delivery of medication to patients who are unable to swallow or accept medication orally.

For patients who have impaired ability to swallow, medications have been administered through a tube passing from the patient's nasal cavity and pharynx into the stomach, referred to as the naso-gastric route or through the mouth. For example, U.S. Pat. No. 4,205,676 describes apparatus employing pumped air to force fluids, such as a liquified food product, into the stomach by way of a naso-gastric tube. Although this patent describes replenishment of "flowable" material supply within containers from which the material is forced by air pressure, it does not provide for administering solid tablets or capsules to patients unable to swallow.

In order to dissolve solid or powdered medications, U.S. Pat. Nos. 708,224, 2,798,488, and 4,306,554 describe syringe units which include separate compartments for the solid and solvent. The compartments are interconnectable so as to enable dissolution of the solid and displacement of the solution. U.S. Pat. No. 3,351,058 describes a two compartment syringe unit for placement of solid within one compartment separated by a frangible membrane in the second compartment having flexible walls for holding a liquid ingredient. In use, sufficient mechanical pressure is applied to the flexible walls of the fluid compartment so that the frangible membrane will be ruptured by internal hydraulic pressure, thereby enabling flow of the liquid ingredient into the compartment holding the solid ingredient to form a solution.

When the prescribed medication is in the form of a pill or tablet, the devices described in these patents require sufficient period of time for complete dissolving of the tablet in solution. While prior pulverization of the tablet, for example with mortar and pestle, can be employed in order to insert a powdered solid into the device described in these patents, the prior pulverization process introduces problems of contamination and inaccuracy in the level of the dosage as well as the inconvenience of additional material transfer.

SUMMARY OF THE INVENTION

In accordance with this invention, these disadvantages are eliminated by enabling pulverization or crushing of a tablet within the same device employed for delivery of the medication to the patient. The device can be disposable to eliminate cleaning or reuse.

The device provides a chamber having a resiliently deformable, peripheral wall with an opening at one end for insertion of a tablet and a removable cap which closes the opening. The wall of the chamber is selectively resilient to allow crushing of the tablet into a powder by repeated, mechanical deformation of the opposing portions of the wall while compressing the tablet and resulting fragments between the deformed wall portions until the desired degree of pulverization is achieved. The powder can then be dissolved within the chamber, for example, by removing the cap and pouring the solvent into the chamber. The cap includes a fitting for connection to a syringe or other fluid dispenser, to enable communication between the syringe and the chamber through the cap. The chamber is also provided with an outlet, and the effluent solution from the chamber is displaced by the action of the coupled syringe when the solution is to be adminstered to the patient through a feeding tube.

The outlet from the chamber can be coupled to a delivery tube which can be passed through the nasal cavity into the stomach of the patient for delivering the medication to a patient who is unable to swallow. The device can also be used for oral administration of medication.

In a preferred embodiment of the device, the fitting on the cap includes a conventional Luer-Lock adapter for convenient, twist coupling to the mating, Luer-Lock nozzle of commercially available syringes.

DESCRIPTION OF THE PREFERRED EMBODIMENT

Figure 1:
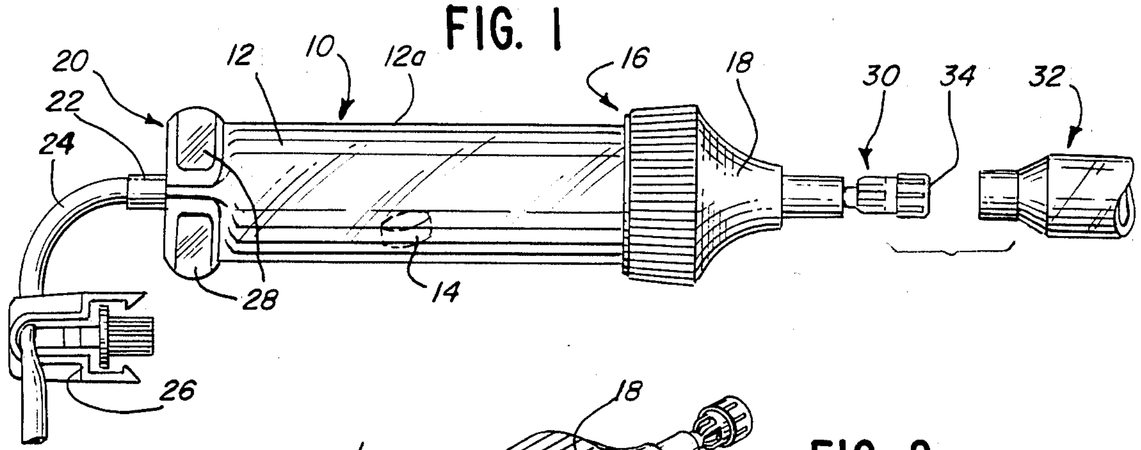
FIG. 1 is a side view of an embodiment of the medication dispensing device according to this invention, illustrating a tablet disposed within a resilient, deformable chamber.

Referring to FIG. 1, an embodiment of the dispensing device of the invention is designated generally by the reference character 10. The device includes a chamber 12 having a resilient deformable peripheral wall **12*a*. The chamber 12 is fabricated from a suitably pliant material, such as elastomeric plastic, and is preferably transparent in order to allow viewing of the content, particularly during crushing of a tablet 14**, as described hereinafter. Suitable elastomeric plastic is commercially available, for example, under the trade names Viaflex, and Tygon ® from U.S. Stoneware Corporation.

Figure 3:
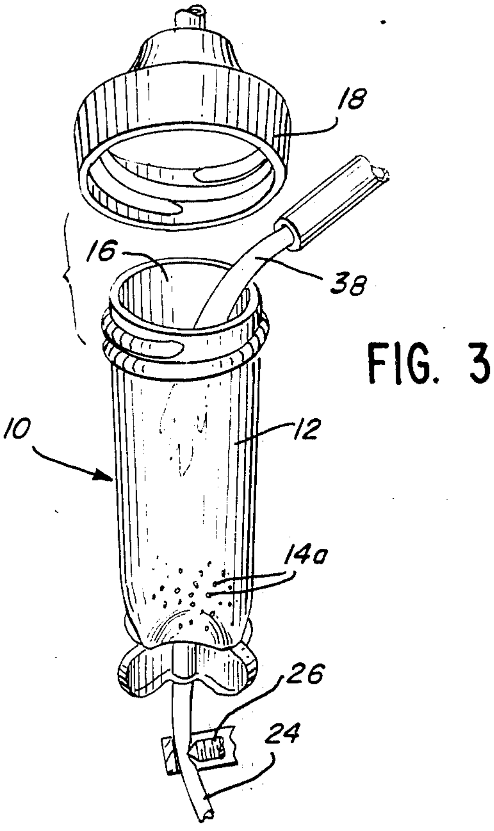
FIG. 3 is a perspective view of the device of FIG. 2 illustrating a cap removed to permit pouring of liquid into the chamber to dissolve the crushed tablet.

In the illustrated embodiment, chamber 12 has a tubular configuration with an opening at one end 16 which can be closed by a removable cap 18 as further illustrated in FIG. 3. The chamber 12 and cap 18 are provided with screw threads, and alternatively, other suitable means such as press fit can be employed for removable closure by the cap 18.

Figure 2:
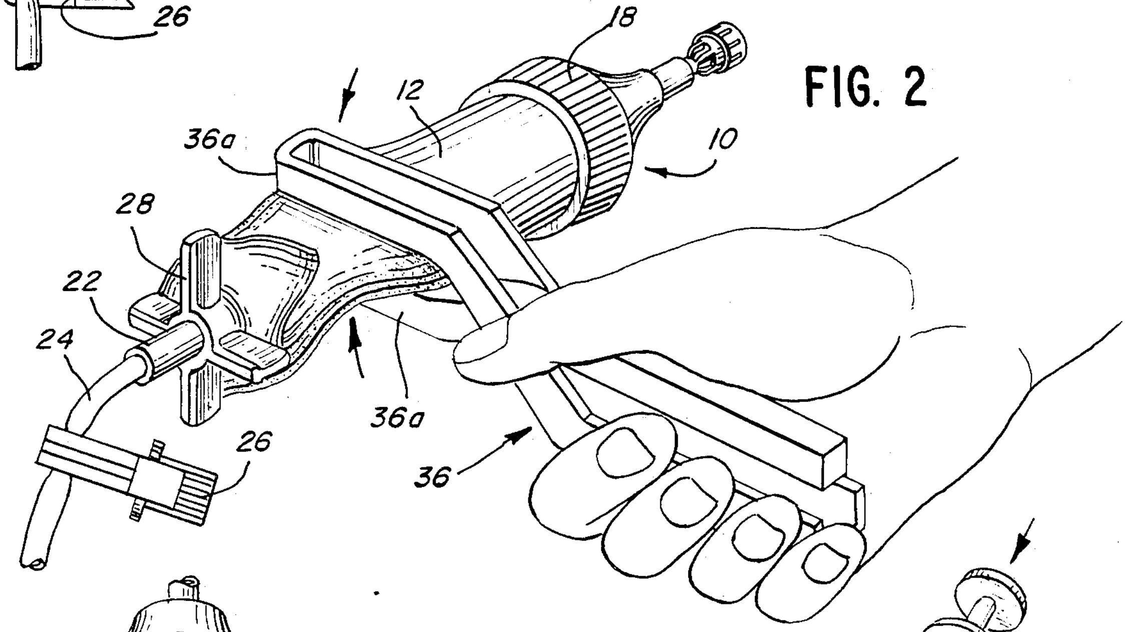
FIG. 2 is a perspective view of the device of FIG. 1 and further illustrating manual crushing of the tablet within the chamber by direct application of plier jaws to compress the opposing walls of the deformable chamber.

Referring again to FIG. 1, the opposite end 20 of the chamber 12 is provided with an outlet 22 which is coupled to a delivery tube 24 for administration of medication from the device 20 to a patient. A crimp clamp 26 is provided on the tube 24 in order to control fluid flow of the medication therethrough. Alternatively, any suitable valve means can be employed for such flow control. As best shown in FIG. 2, the outlet 22 can be provided with gripping ribs 28 which can be formed integral with the chamber 12. Such gripping ribs are merely an optional convenience, and alternatively, the outlet 22 can be formed simply as an integral tapering in the wall of the chamber 12. An adapter (not shown) can be provided on the tube 24, preferably downstream from clamp 26, for coupling the tube 24 to any desired extension tube.

Referring again to FIG. 1, the cap 18 is provided with a fitting designated generally by reference character 30 for coupling the cap 18 to the nozzle of a syringe 32. A removable plug 34 is provided to close the opening of the fitting 30 when the syringe 32 is not coupled thereto. Preferably, the fitting 30 and syringe 32 are provided with a conventional "Luer-Lock" adapter and nozzle, respectively, for convenient coupling of commercially available syringes to the cap 18 and fluid communication thereof with the chamber 12 through the cap.

Figure 4:
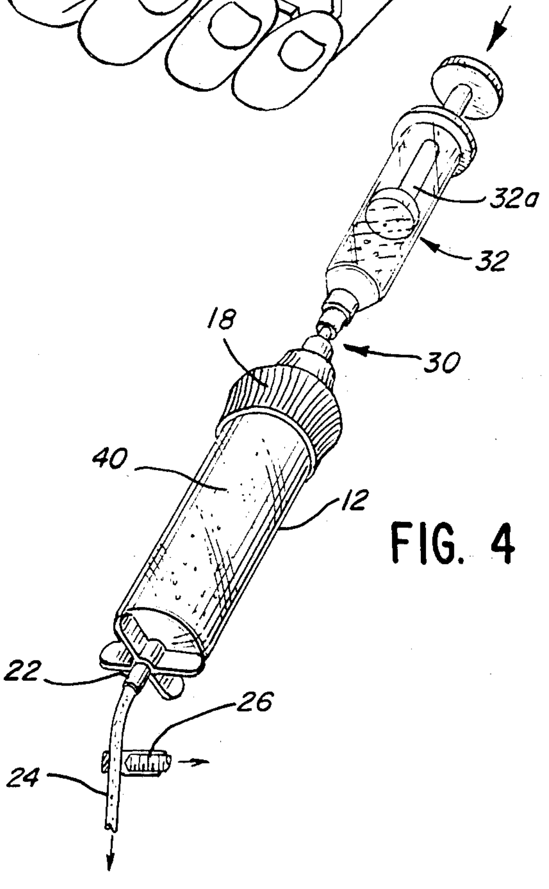
FIG. 4 is a perspective view of the device of FIG. 3 illustrating a syringe unit connected through a conventional "Luer-Lock" fitting on the cap and the displacement of the solution from the chamber through the tube coupled to the outlet from the chamber for administration to a patient.

Use of the dispensing device 10 to prepare a tablet 14 for administration to a patient will now be described with reference to FIGS. 2 to 4. After removing cap 18 from chamber 12 and placement of tablet 14 therein, the clamp 26 and tube 24 are closed and the plugged cap 18 is replaced on the chamber 12. Thereafter, the tablet 14 is crushed by compressing the opposing portions of the resilient chamber wall 12*a*. As illustrated in FIG. 2, a pair of pliers 36 having flat-faced jaws 36*a* is used to repeatedly compress the walls of the chamber until the pinched tablet is crushed into a generally powdered form of desired uniformity which can be readily dissolved. Obviously, any suitable tool can be employed to compress chamber 12 and crush the tablet 14, provided that the chamber wall is not ruptured.

Referring now to FIG. 3, after crushing the tablet 14 into powder 14*a*, the cap 18 can be removed from the chamber 12 so that water 38 or other suitable solvent for medication can be poured into the chamber 12 to dissolve the powder 14*a*. Thereafter, the cap 18 is replaced on the chamber 12, and if necessary, the entire device 10 can be shaken to promote the dissolution.

The resulting solution 40 is administered to the patient who cannot swallow by passing the extension of tube 24 through the patient's nasal cavity into the stomach. Referring to FIG. 4, the loaded syringe 32 is then coupled to the fitting 30 after which the clamp 26 is opened. The effluent solution 40 from chamber 12 is then delivered through the open tube 24 by depressing the plunger 32*a* of the syringe 32 to force displacement of the solution 40 from the chamber 12 through the outlet 22.

The in-line crushing and dissolution chamber of the invention not only eliminates loss or dosage inaccuracy in material transfer of tablets pulverized before placement into prior art devices, but in addition, contamination during the previously required handling of crushed tablets is also eliminated. Coupling of a syringe directly to the crushing and dissolution chamber enables the solution to be displaced directly from the chamber to the patient for administration of the medication by either naso-gastric or oral route.

Variations in the size and structural features of cooperating parts and in materials used may occur to the skilled artisan without departing from the crux of the invention, the scope of which is set forth in the claims hereto appended.

We claim:

1. A device for crushing, dissolving in liquid and dispensing medication initially in tablet form, comprising:

A. a dispenser including resiliently deformable, peripheral walls defining a chamber within said dispenser, an opening at one end thereof for insertion of a medicament tablet within said chamber;

B. a removable cap closing said opening, and including a fitting for selectively coupling said dispenser and said chamber to a solvent source to enable communication between said chamber and said solvent source through said cap;

C. said chamber having an outlet spaced from said opening, and said walls of said dispenser being of sufficient length and sufficiently resilient to enable repeated deformation of opposing portions of the walls into contact with said tablet and each other for crushing of said tablet to form a powder for dissolution within said chamber by said solvent and subsequent administration of the resulting solution to a patient during discharge of said solution from said outlet.

2. The device as claimed in claim 1, further including a delivery tube coupled to said outlet and valve means for controlling flow of said solution through said tube.

3. The device as claimed in claim 1, in which said fitting includes a luer type adapter for coupling to a mating nozzle formed on said dispenser.

4. The device as claimed in claim 3, wherein said dispenser comprises syringe means having said nozzle coupled to said adapter.

5. The device as claimed in claim 1 in which said outlet is formed by an integral, tapered section of said walls.

6. The device as claimed in claim 1, further including crushing means for deforming said dispenser walls to effect said crushing without rupturing said walls.

7. A method for crushing and dispensing medication in tablet or like solid form, comprising:

A. inserting a tablet into a chamber having resiliently deformable, peripheral walls;

B. repeatedly deforming said walls with sufficient pressure to contact each other and crush said tablet into a generally powdered form therebetween;

C. introducing a solvent into said chamber after said tablet has been crushed to powder and dissolving said crushed tablet powder to form a solution thereof within said chamber; and D. displacing said solution from said chamber for administration of the solution to a patient.

* * * * *